(12) United States Patent
Münter et al.

(10) Patent No.: US 6,329,384 B1
(45) Date of Patent: Dec. 11, 2001

(54) ENDOTHELIN ANTAGONIST AND RENIN-ANGIOTENSIN SYSTEM INHIBITOR AS A COMBINED PREPARATION

(75) Inventors: Klaus Münter; Michael Kirchengast, both of Mannheim; Horst Korioth, Bammental, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/508,993

(22) PCT Filed: Sep. 10, 1998

(86) PCT No.: PCT/EP98/05773
§ 371 Date: Mar. 20, 2000
§ 102(e) Date: Mar. 20, 2000

(87) PCT Pub. No.: WO99/16445
PCT Pub. Date: Apr. 8, 1999

(30) Foreign Application Priority Data

Sep. 26, 1997 (DE) ................................ 197 42 717
Sep. 30, 1997 (DE) ................................ 197 43 141

(51) Int. Cl.[7] ................................ A61K 31/505

(52) U.S. Cl. ................................ 514/274
(58) Field of Search ................................ 514/274

(56) References Cited

U.S. PATENT DOCUMENTS 5,696,116   12/1997   Clozel .

FOREIGN PATENT DOCUMENTS

| 617 001 | 9/1994 | (EP) . |
|---|---|---|
| 96/19233 | 6/1996 | (WO) . |
| 96/22978 | 8/1996 | (WO) . |
| 98/09953 | 3/1998 | (WO) . |
| 98/24482 | 6/1998 | (WO) . |
| 98/27070 | 6/1998 | (WO) . |

OTHER PUBLICATIONS

J. Phar, vol. 278, No. 3, Cameron et al. (1996).
A/H, Apr. 1998, vol. 11, No. 4, Part 3, Brunner (1998).

*Primary Examiner*—Raymond Henley, III
(74) *Attorney, Agent, or Firm*—Keil & Weinkauf

(57) ABSTRACT

A combination of endothelin antagonists and RAS inhibitor is described. The combination is suitable for controlling diseases.

4 Claims, No Drawings

ENDOTHELIN ANTAGONIST AND RENIN-ANGIOTENSIN SYSTEM INHIBITOR AS A COMBINED PREPARATION

This is a 371 of PCT/EP98/05773 filed Sep. 10, 1998.

The present invention relates to novel pharmaceutical combination products suitable for treating cardiovascular disorders and comprising an inhibitor of the renin-angiotensin system (RAS inhibitor) and an endothelin antagonist.

Combination products suitable for treating cardiovascular disorders and comprising an inhibitor of the renin-angiotensin system (RAS inhibitor) and an endothelin antagonist have been disclosed (EP-A-634,175, EP-A-617, 001). However, the effect of these mixtures of active ingredients is unsatisfactory.

Combinations with improved properties have now been found.

The present invention relates to a combination of an endothelin antagonist of the formula I

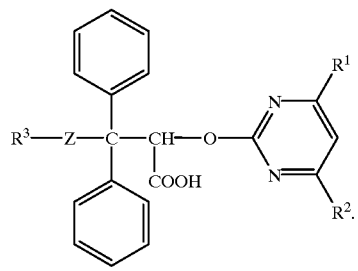

I in which the substituents have the following meanings:

$R^1$ $C_1$–$C_4$-alkyl, $C_1$–$C_4$-alkoxy;

$R^2$ $C_1$–$C_4$-alkyl, $C_1$–$C_4$-alkoxy;

$R^3$ $C_1$–$C_8$-alkyl which may be substituted by a phenyl radical which in turn may be substituted by one or two $C_1$–$C_4$-alkoxy radicals, Zz oxygen or a single bond, and an RAS inhibitor.

Preferred endothelin antagonists are those compounds of the formula I in which the substituents have the following meanings:

$R^1$: $C_1$–$C_2$-alkyl, $C_1$–$C_2$-alkoxy $R^2$: $C_1$–$C_2$-alkyl, $C_1$–$C_2$-alkoxy $R^3$: $C_1$–$C_2$-alkyl which may be substituted by a phenyl radical which in turn may be substituted by one or two $C_1$–$C_2$-alkoxy radicals, Z: oxygen or a single bond.

Particularly suitable endothelin antagonists are the following compounds:

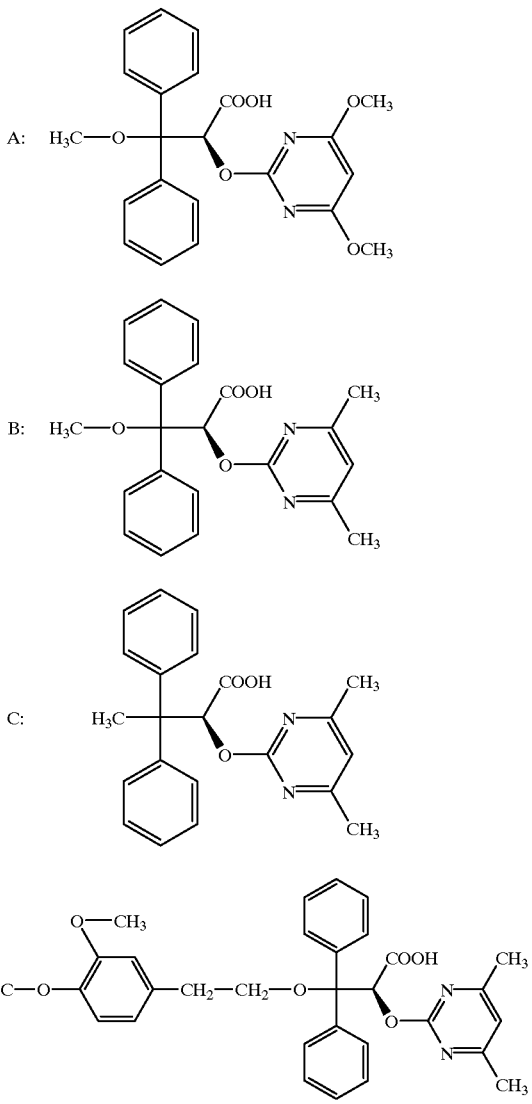

Suitable inhibitors of the renin-angiotensin system are in particular angiotensin II antagonists and very particularly ACE inhibitors.

ACE inhibitors suitable for the purpose of the present invention are alacepril, benazepril, captopril, cilazapril, cilazaprilat, delapril, enalapril, enalaprilat, fosinopril, lisinopril, perindopril, quinapril, ramipril, spirapril, trandolapril and zofenopril. Among these, preference is given to ramipril and, in particular, to trandolapril.

Angiotensin II antagonists suitable for the purpose of the present invention are: losartan, the potassium salt of
  2-butyl-4-chloro-1-[[2'-(1H-tetrazol-5-yl)[1,1'-biphenyl]-4-yl]-methyl-1-H-imidazole-5-methanol; valsartan, N-(1-oxopentyl)-N-[[2'-(1H-tetrazol-5-yl)[1,1'-biphenyl-4-yl]methyl-L-valine;
  candesartan, 2-ethoxy-1-[[2'-(1H-tetrazol-5-yl)[1,1-biphenyl]-4-yl]methyl]-1-H-benzimidazole-7-carboxylic acid;
  4'-[(2-n-butyl-6-cyclohexylaminocarbonylamino-benzimidazol-1-yl)-methyl]biphenyl-2-carboxylic acid;
  2-n-butyl-1-[4-(6-carboxy-2,5-dichlorobenzoylamino)benzyl]-6-N-(methylaminocarbonyl)-n-pentylaminobenzimidazole;

4'-[(1,4'-dimethyl-2'-propyl-[2,6'-bi-1-H-benzimidazol]-1'-yl)-methyl]-[1,1'-biphenyl]-2-carboxylic acid;

4-(pentafluoroethyl)-2-propyl-1-[[2'-(1H-tetrazol-5-yl)[1,1'-biphenyl]-4-yl]methyl]-1-H-imidazole-5-carboxylic acid;

4'-[[2-butyl-4-chloro-5-(hydroxymethyl)-1-H-imidazol-1-yl]methyl]-[1,1'-biphenyl]-2-carboxylic acid;

2-ethyl-5,6,7,8-tetrahydro-4-([2'-(-H-tetrazol-5-yl)biphenyl-4-yl]methoxy)quinoline;

2-ethyl-4-[(2'-(1H-tetrazol-5-yl)biphenyl-4-yl)methoxy]quinoline hydrochloride;

1-[[3-bromo-2-(2-(1H-tetrazol-5-yl)phenyl)-5-benzofuranyl]-methyl]-2-butyl-4-chloro-1H-imidazole-5-carboxylic acid;

1-[[3-bromo-2-[2-[(trifluoromethyl)sulfonyl]amino]phenyl-5-benzofuranyl]methyl]-4-cyclopropyl-2-ethyl-1-H-imidazole-5-carboxamide;

5,7-dimethyl-2-ethyl-3-(2'-(1H-tetrazol-5-yl)(1,1'-biphenyl)-4-yl)-methyl)-3H-imidazo-(4,5-b)pyridine;

5-[4'-(3,5-dibutyl-1,2,4-triazol-1-ylmethyl)biphenyl-2-yl]-1H-tetrazole;

1,4-dibutyl-3-[2'-(1H-tetrazol-5-yl)biphenyl-4-ylmethyl]-2,3-dihydro-1H-imidazol-2-one;

2-n-butyl-4-spirocyclopentane-1-[(2'-(1H-tetrazol-5-yl)biphenyl-4-yl)methyl]-2-imidazolin-5-one;

(E)-α-[[2-butyl-1-[(4-carboxyphenyl)methyl]-1-Himidazol-5-yl]-methylene]-2-thiophenepropanoic acid;

2-ethoxy-1-[[2'-(1H-tetrazol-5-yl)[1,1'-biphenyl]-4-yl]methyl]-1H-benzimidazole-7-carboxylic acid 1-[[(cyclohexyloxy)carbonyl]oxy]ethyl ester;

2-propyl-4-[(3-trifluoroacetyl)pyrrol-1-yl]-1-[[2'-(2H-tetrazol-5-yl)[1,1'-biphenyl]-4-yl]methyl]-1H-imidazole-5-carboxylic acid; and the potassium salt of 2,7-diethyl-5-[[2'-(1H-tetrazol-5-yl)[1,1'-biphenyl]-4-yl]methyl]-5H-pyrazolo[1,5-b][1,2,4]-triazole.

Disorders associated with vasoconstriction or other biological effects of endothelin and/or angiotensin II which may be particularly mentioned are the control or prevention of coronary disorders, cardiovascular disorders such as hypertension, heart failure, ischemia (in the heart, brain, gastrointestinal tract, liver and/or kidney) or vasospasms. Further examples of disorders which can be treated are renal insufficiency and renal failure, dialysis, subarachnoid hemorrhage, Raynaud's syndrome, portal hypertension and pulmonary hypertension, and the treatment of gastric and duodenal ulcers and of leg ulcer in which vasoconstriction is involved. They can also be employed for atherosclerosis and for preventing restenosis after balloon-induced vasodilatation. Finally, the endothelin concentration is increased in the bronchial secretion of patients with asthma. Increased endothelin levels in blood plasma are also found during migraine attacks. The combination can therefore also be used in these two cases.

On administration of the combination according to the invention there is a considerable, more than additive, enhancement of the blood pressure-lowering properties and of the duration of action compared with the single substances. The doses of the individual active ingredients can thus be considerably reduced. This means that fewer side effects are to be expected on administration.

The ratio by weight of inhibitor of the renin-angiotensin system to endothelin antagonist is normally in the range from 50:1 to 1:500, preferably 10:1 to 1:100 and, in particular, 2:1 to 1:50.

The combinations according to the invention are generally administered orally, for example in the form of tablets, lacquered tablets, sugar-coated tablets, hard and soft gelatin capsules, solutions, emulsions or suspensions. However, administration can also take place rectally, for example in the form of suppositories, or parenterally, for example in the form of injection solutions. The active ingredients can be administered in the form of products which contain both active ingredients together, such as tablets or capsules, or separately as ad-hoc combination of single substances, which can be administered concurrently or sequentially.

To produce tablets, lacquered tablets, sugar-coated tablets and hard gelatin capsules it is possible to process a combination according to the invention with pharmaceutically inert, inorganic or organic excipients. Excipients which can be used for tablets, sugar-coated tablets and hard gelatin capsules are lactose, corn starch or derivatives thereof, talc, stearic acid or salts thereof. Excipients suitable for such gelatin capsules are vegetable oils, waxes, fats, semisolid and liquid polyols.

Excipients suitable for producing solutions and syrups are, for example, water, polyols, sucrose, invert sugar, glucose and the like. Excipients suitable for injection solutions are water, alcohols, polyols, glycerol, vegetable oils. Excipients suitable for suppositories are natural or hardened oils, waxes, fats, semiliquid or liquid polyols and the like.

The pharmaceutical preparations may additionally contain preservatives, solubilizers, stabilizers, wetting agents, emulsifiers, sweeteners, colorants, flavorings, salts to alter the osmotic pressure, buffers, coating agents and/or antioxidants.

The following tests show the unexpectedly advantageous properties of the combinations according to the invention:

The test substance was administered orally as capsule to chronically instrumented male Beagle dogs (about 14 kg) in a crossover design. The capsules contained either nothing (control n=10), trandolapril (2 mg/kg; N=10), compound A (10 mg/kg, N=10) or combinations of trandolapril+compound A (2+10 mg/kg; N=10; and 2+0.5 mg/kg; N=5). A washout period of at least one week was left between the individual administrations. The change in blood pressure was recorded for 6 h. The systolic (SAP) and diastolic (DAP) blood pressure in the abdominal artery [mmHg] were measured, from which the mean arterial blood pressure (MAP) was determined. The heart rate [min$^{-1}$] was calculated from the systolic peak of the blood pressure signal.

Table 1 shows that there is no fall in blood pressure in the control group and in the group treated with trandolapril. A slight fall in blood pressure is to be seen with compound A and is significant at some time points. The combination of trandolapril with the ET antagonist compound A (2+10 mg/kg) shows a marked fall in blood pressure, which is still pronounced even in the $2^{nd}$ combination group with the smaller proportion of $ET_A$ antagonist (only 0.5 mg/kg in place of 2 mg/kg).

TABLE 1

Changes in mean arterial blood pressure (MAP, mmHg) in conscious normotensive dogs after administration of various substances, means shown

| | N | Initial | 1 h | 2 h | 3 h | 4 h | 5 h | 6 h |
|---|---|---|---|---|---|---|---|---|
| Placebo | 10 | 103 | 3 | 2 | 2 | 1 | 1 | 1 |
| Compound A 10 mg/kg | 10 | 99.6 | −5.9 | −8.9 | −9 | −9.1 | −8.4 | −8.2 |
| Trandolapril 2 mg/kg | 10 | 99.8 | −4.1 | −2.9 | 0.9 | 1.7 | −0.1 | 0.2 |

TABLE 1-continued

Changes in mean arterial blood pressure (MAP, mmHg) in conscious normotensive dogs after administration of various substances, means shown

|  | N | Initial | 1 h | 2 h | 3 h | 4 h | 5 h | 6 h |
|---|---|---|---|---|---|---|---|---|
| Combination of A + T 2 + 10 mg/kg | 10 | 96 | −18.7 | −30.9 | −30.8 | −30.3 | −28.6 | −23.6 |
| Combination of A + T 0.5 + 2 mg/kg | 5 | 97.1 | −3.8 | −12.7 | −14.7 | −11.5 | −10.4 | −4.6 |

There is no change in heart rate in the control group over the observation period (Table 2). With compound A there is an increase of about 11 beats in the rate, which may be interpreted as reflex response to the fall in blood pressure pressure. Trandolapril likewise leads to an increase in the rate, despite the lack of an effect on the blood pressure, and this is even more pronounced in the combination groups.

TABLE 2

Changes in heart rate (min$^{-1}$) in conscious normotensive dogs after administration of various substances, means shown

|  | N | Initial | 1 h | 2 h | 3 h | 4 h | 5 h | 6 h |
|---|---|---|---|---|---|---|---|---|
| Control | 10 | 71 | −3.3 | 2.3 | −1.7 | −4.5 | −2.5 | −5.9 |
| Compound A 10 mg/kg | 10 | 73.8 | 3.7 | 11.1 | 10.2 | 8 | 8.3 | 3.1 |
| Trandolapril 2 mg/kg | 10 | 69 | 6.7 | 15.5 | 13 | 10 | 10.3 | 7.5 |
| Combination of A + T 2 + 10 mg/kg | 10 | 70.6 | 15.6 | 25.4 | 27.2 | 24.1 | 21.6 | 10.5 |
| Combination of A + T 0.5 + 2 mg/kg | 5 | 60.3 | 11.1 | 18.8 | 15.1 | 13.2 | 11.1 | 8.3 |

The following examples illustrate the invention.

EXAMPLE 1

Lacquered Tablets of the Following Composition were Produced:

| Compound A | 200.0 mg |
|---|---|
| Trandolapril | 2.0 mg |
| Lactose, anhydrous | 30.0 mg |
| Microcrystalline cellulose | 30.0 mg |
| Polyvinylpyrrolidone | 20.0 mg |
| Magnesium stearate | 5.0 mg |
| Polyethylene glycol 6000 | 0.8 mg |
| Iron oxide, yellow | 1.2 mg |
| Titanium dioxide | 0.3 mg |
| Talc | 0.7 mg |

Compound A, trandolapril, the lactose, the cellulose and the polyvinylpyrrolidone are wet-granulated and dried. The sieved granules are mixed with the magnesium stearate, and the mixture is then ready for compression to oval tablet cores each of 290.0 mg. The cores are then coated with lacquer until the lacquered tablets have reached a final weight of 300 mg.

EXAMPLE 2

Production of Hard Gelatin Capsules of the Following Composition:

| Compound A | 250.0 mg |
|---|---|
| Ramipril | 2.5 mg |
| Lactose, cryst. | 18.0 mg |
| Polyvinylpyrrolidone | 15.0 mg |
| Microcrystalline cellulose | 17.5 mg |
| Sodium carboxymethyl starch | 10.0 mg |
| Talc | 9.0 mg |
| Magnesium stearate | 3.0 mg |

The first five ingredients are wet-granulated and dried. The granules are mixed with the sodium carboxymethyl starch, the talc and the magnesium stearate, and the mixture is packed into size 1 hard gelatin capsules.

We claim:

1. A combination of an endothelin antagonist of the formula I

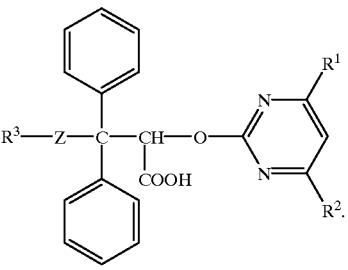

in which the substituents have the following meanings:

$R^1$ $C_1$–$C_4$-alkyl, $C_1$–$C_4$-alkoxy;

$R^2$ $C_1$–$C_4$-alkyl, $C_1$–$C_4$-alkoxy;

$R^3$ $C_1$–$C_8$-alkyl which may be substituted by a phenyl radical which in turn may be substituted by one or two $C_1$–$C_4$-alkoxy radicals, z oxygen or a single bond, and an RAS inhibitor.

2. A pharmaceutical preparation comprising a combination as claimed in claim 1.

3. The production of a pharmaceutical preparation, which comprises converting a mixture of an RAS inhibitor and an endothelin antagonist as set forth in claim 1 into a pharmaceutical dosage form.

4. A method for treating, in a patient, disorders associated with vasoconstriction or other biological effects of endothelin and/or angiotensin II, which comprises administering to said patient, either concurrently, separately or sequentially, an effective amount of a combination of an RAS inhibitor and an endothelin antagonist as set forth in claim 1, or of a pharmaceutical preparation comprising an RAS inhibitor and an endothelin antagonist as set forth in claim 1.

* * * * *